US009765295B2

(12) United States Patent
Park et al.

(10) Patent No.: US 9,765,295 B2
(45) Date of Patent: Sep. 19, 2017

(54) COMPOSITION FOR CULTURING SANAL AND SANAL CULTURING METHOD USING THE SAME

(71) Applicants: Samsung Electronics Co., Ltd., Suwon-si, Gyeonggi-do (KR); Advanced Institutes of Convergence Technology (AICT), Suwon-si, Gyeonggi-do (KR); Seoul National University R&DB Foundation, Seoul (KR)

(72) Inventors: Tai Hyun Park, Seoul (KR); Hwi Jin Ko, Seoul (KR); Sang Yeob Jeong, Seoul (KR); Kwangsup Soh, Suwon-si (KR); Minseok Kim, Yongin-si (KR); Youngjun Koh, Yongin-si (KR); Jaeyoung Kim, Seoul (KR)

(73) Assignees: SAMSUNG ELECTRONICS CO., LTD., Suwon-si (KR); ADVANCED INSTITUTES OF CONVERGENCE TECHNOLOGY (AICT), Suwon-si (KR); SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 234 days.

(21) Appl. No.: 14/796,836

(22) Filed: Jul. 10, 2015

(65) Prior Publication Data

US 2016/0115442 A1   Apr. 28, 2016

(30) Foreign Application Priority Data

Oct. 27, 2014 (KR) .................. 10-2014-0146435

(51) Int. Cl.
*C12N 5/071* (2010.01)
*C12N 5/078* (2010.01)

(52) U.S. Cl.
CPC ......... *C12N 5/0602* (2013.01); *C12N 5/0634* (2013.01); *C12N 2500/32* (2013.01); *C12N 2500/34* (2013.01); *C12N 2501/81* (2013.01); *C12N 2501/905* (2013.01)

(58) Field of Classification Search
None
See application file for complete search history.

(56) References Cited

U.S. PATENT DOCUMENTS 8,765,413 B2   7/2014   Joosten et al.
8,785,194 B2   7/2014   Gorfien et al.

FOREIGN PATENT DOCUMENTS

KR   10-20050049578 A   5/2005
KR   10-0666595 B1   1/2010

OTHER PUBLICATIONS

Kang K.A. (2016) Chronological Review on Scientific Findings of Bonghan System and Primo Vascular System. In: Luo Q., Li L., Harrison D., Shi H., Bruley D. (eds) Oxygen Transport to Tissue XXXVIII. Advances in Experimental Medicine and Biology, vol. 923. Springer, Cham; 2016: 301-309.*
Kang et al, "Technical Challenges in Current Primo Vascular System Research and Potential Solutions" Journal of Acupuncture and Meridian Studies, 2016, vol. 9 No. 6, pp. 297-306.*
Lee et al "Primo Vascular System in Human Umbilical Cord and Placenta" Journal of Acupuncture and Meridian Studies, 2014, vol. 7 No. 6, pp. 291-297.*
Ogay et al, "Identification and characterization of small stem-like cells in the primo vascular system of adult animals" In: Soh KS, Kang KA, Harrison DH, eds. The Primo Vascular System: Its Role in Cancer and Regeneration. New York: Springer; 2012: 149-156.*
Park et al, "Expression of Stem Cell Markers in Primo Vessel of Rat" Evidence-Based Complemntary and Alternative Medicine, 2013, Article ID 438079, 6 pages.*
Stefanov et al, "The Primo Vascular System as a New Anatomical System" Journal of Acupuncture and Meridian Studies, 2013, vol. 6, No. 6, pp. 331-338.*
Simonsen et al., Isolation and expression of an altered mouse dihydrofolate reductase cDNA, *Proc. Natl. Acad. Sci. U.S.A.*, 80: 2495-2499 (1983).
Kwon et al., "Scanning probe microscopy study of microcells from the organ surface Bonghan corpuscle", *Applied Physics Letters*, 90(17): 1-3, No. 173903 (2007).
Kim Bong Han, "Kyungrak System and Theory of Sanal Theory," Proceedings of the Academy of Kyungrak of the DPRK, Medical Science Press, No. 2, pp. 71-73, Apr. 15, 1965.

* cited by examiner

*Primary Examiner* — Allison Fox
(74) *Attorney, Agent, or Firm* — Leydig, Voit & Mayer, Ltd.

(57) ABSTRACT

Provided are a sanal culturing composition and a method for culturing sanal using the same.

12 Claims, 8 Drawing Sheets

COMPOSITION FOR CULTURING SANAL AND SANAL CULTURING METHOD USING THE SAME

RELATED APPLICATION

This application claims the benefit of Korean Patent Application No. 10-2014-0146435, filed on Oct. 27, 2014, in the Korean Intellectual Property Office, the entire disclosure of which is hereby incorporated by reference.

BACKGROUND

1. Field

The present disclosure relates to a sanal culturing composition, and a sanal culturing method using the same.

2. Description of the Related Art

Various clinical studies have verified the effects of acupuncture treatment using the meridian system and acupuncture points, which is one of the fundamental theories of Korean medicine. Moreover, the mechanisms of treatment through the nervous and endocrine systems and gene expression are being revealed one after another. Recently, a novel structure related to the meridian system was discovered by Asian researchers, with the form of thin tube bundles inside blood vessels and lymphatic vessels and not known in conventional anatomy. This novel structure has been identified to not only connect an organ to another organ but also connect an organ to the body surface. In addition, such a meridian circulation duct is called a primo duct or a Bong Han duct, and these primo ducts suggest the possibility of the primo circulatory system, or primo vascular system (PVS), being a novel circulatory system which may be considered as the third circulatory system of the human body.

Sanal (or primo microcell), which flows in a primo duct, is a small cell comprising DNA and proteins. It was recently found that large quantities of immune cells are present in a primo duct, where stem cell markers were also observed. Furthermore, a possibility has been raised that stem cells related to cancer may be present in PVS. Such studies demonstrate that research on PVS goes beyond the simple anatomical level of elucidating the existence and location of the system, and that there is active ongoing research related to tissue regeneration and the treatment of diseases, such as cancer and diabetes. Consequently, much interest is focused on the function of sanals present in PVS. However, a problem remains in that it is difficult to collect sanals present in PVS and the amount of collected sanals is insufficient.

Thus, there is a need for developing a culture fluid for stably culturing sanal, and a sanal culturing method using the same.

SUMMARY

A sanal culturing composition is provided.
A sanal culturing method is provided.

DETAILED DESCRIPTION

Figure 1:
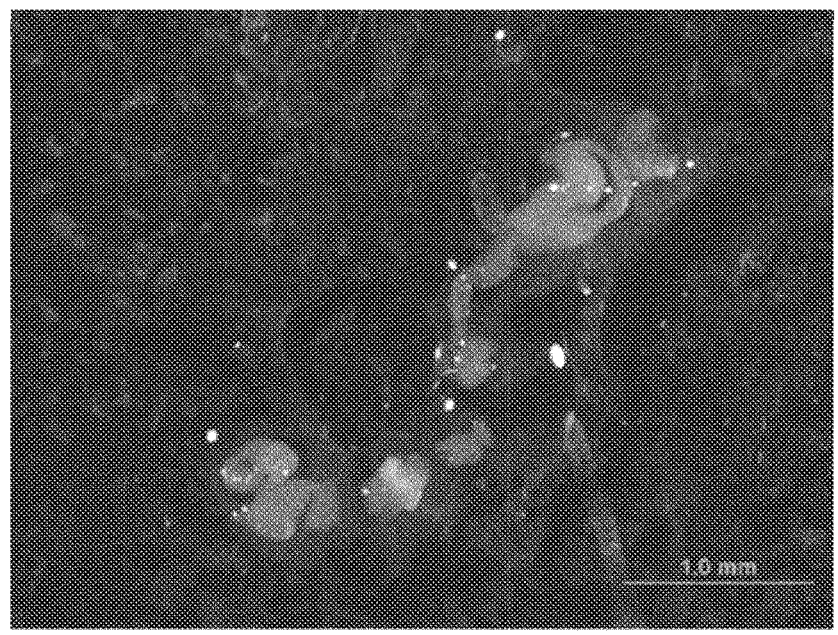
FIG. 1 is a photograph of primo ducts and primo nodes obtained from an organ surface.

An embodiment of the present disclosure provides a sanal culturing composition comprising lysine, taurine, hyaluronic acid, or a combination thereof.

Lysine is an amino acid with the chemical formula $H_2NCH_2CH_2CH_2CH_2CH(NH_2)COOH$. The lysine may be, for example, L-lysine. The amount of the lysine used may vary according to the concentration ratio of the other elements of the sanal culturing composition. In some embodiments, the lysine may be present in the sanal culturing composition at a concentration of about 150 mg/L to about 300 mg/L, about 160 mg/L to about 290 mg/L, about 170 mg/L to about 280 mg/L, about 180 mg/L to about 270 mg/L, about 190 mg/L to about 260 mg/L, about 200 mg/L to about 250 mg/L, about 210 mg/L to about 240 mg/L, or about 220 mg/L to about 230 mg/L. Taurine is 2-aminoethanesulfonic acid. The taurine may be, for example, L-taurine. The amount of taurine used may vary according to the concentration ratio of the other elements of the sanal culturing composition. In some embodiments, the taurine may be present in the sanal culturing composition at a concentration of about 100 mg/L to about 300 mg/L, about 110 mg/L to about 290 mg/L, about 120 mg/L to about 280 mg/L, about 130 mg/L to about 270 mg/L, about 140 mg/L to about 260 mg/L, about 150 mg/L to about 250 mg/L, about 160 mg/L to about 240 mg/L, about 170 mg/L to about 230 mg/L, about 180 mg/L to about 220 mg/L, about 180 mg/L to about 210 mg/L, about 180 mg/L to about 200 mg/L, or about 180 mg/L to about 190 mg/L. Hyaluronic acid is a glycosaminoglycan having a structure in which the two types of sugar, glucuronic acid and N-acetylglucosamine, are repeated. The amount of hyaluronic acid used may vary according to the concentration ratio of the other elements of the sanal culturing composition. In some embodiments, the hyaluronic acid may be present in the sanal culturing composition at a concentration of about 1 mg/L to about 5 mg/L, about 1.5 mg/L to about 4.5 mg/L, about 2 mg/L to about 4 mg/L, about 2 mg/L to about 3.5 mg/L, about 2 mg/L to about 3.0 mg/L, or about 2.5 mg/L.

The term "sanal" refers to a living cell, and is also called a primo microcell. Sanal is usually spherical in shape, but sometimes may be oval shaped. Sanal is usually about 1.2~1.5 μm in size, but can range from 0.8 to 2.4 μm. When Sanal is examined under the phase contrast microscope, it consists of two parts, dark and pale parts. The dark part is mostly located in the center, which is assumed to be the nucleus of the Sanal. The pale parts which remain are observed to be cytoplasm of Sanal (Kyungrak System and Theory of Sanal Theory, Kim Bong Han, pp. 71-73, Apr. 15, 1965; Applied physics letters, vol. 90, Issue 17, id. 173903, 2007). Sanal is known to comprise not only DNA but also proteins. Sanal is a small cell comprising DNA chromatin, flows through a primo duct or Bong Han duct, and is also present in a primo node, which is a nodular body lying between one primo duct and another primo duct. Primo ducts and primo nodes together form the primo vascular system (PVS). PVS can be divided into four types of systems: an internal primo system present in blood vessels, lymphatic vessels, and the inner cavities of the heart; an internal-external primo system distributed primarily over the surface of internal organs; an external primo system running along blood vessels or nerves; and a primo system distributed in nervous tissue. The sanal may be a sanal obtained from a primo duct or a primo node in a primo system. The primo duct or primo node may be located on the surface of an internal organ. The internal organ may be the large intestine.

The term "culturing composition" refers to a composition for providing nutrients to a proliferative cell or microcell. The sanal culturing composition may be a composition for culturing sanal. The culturing composition may be stored as powder for storage, or may be suspended in water, a buffer solution, or the like, for culture. The sanal culturing composition may further comprise essential and non-essential amino acids, vitamins, energy source, lipids, and trace elements necessary for the proliferation or survival of sanal. In addition, the sanal culturing composition may further comprise a component, including hormones and growth factors, for increasing the proliferation or survival of sanal to be above the minimum rate.

The sanal culturing composition may further comprise hydroxyproline, adrenalin, noradrenaline, a reducing sugar, or a combination thereof.

Hydroxyproline is a non-proteinogenic amino acid. The hydroxyproline may be, for example, L-hydroxyproline. The amount of hydroxyproline used may vary according to the concentration ratio of the other elements of the sanal culturing composition. In some embodiments, the hydroxyproline may be present in the sanal culturing composition at a concentration of about 1 mg/L to about 10 mg/L, about 1 mg/L to about 9 mg/L, about 1 mg/L to about 8 mg/L, about 1 mg/L to about 7 mg/L, about 1 mg/L to about 6 mg/L, about 1 mg/L to about 5 mg/L, about 1 mg/L to about 4 mg/L, about 1 mg/L to about 3 mg/L, or about 1 mg/L to about 2 mg/L.

Adrenalin is a hormone of adrenal medulla, and is a compound represented by the chemical formula $C_9H_{13}NO_3$. Adrenalin also called epinephrine. The amount of adrenalin used may vary according to the concentration ratio of the other elements of the sanal culturing composition. In some embodiments, the adrenalin may be present in the sanal culturing composition at a concentration of about 50 ng/mL to about 100 ng/mL, about 55 ng/mL to about 95 ng/mL, about 60 ng/mL to about 90 ng/mL, about 65 ng/mL to about 85 ng/mL, about 70 ng/mL to about 80 ng/mL, or about 75 ng/mL to about 80 ng/mL.

Noradrenaline is a hormone, and is a compound represented by the chemical formula $C_8H_{11}NO_3$. Noradrenaline is one of the stress hormones released into blood from the adrenal gland. The amount of noradrenaline used may vary according to the concentration ratio of the other elements of the sanal culturing composition. In some embodiments, the noradrenaline may be present in the sanal culturing composition at a concentration of about 100 ng/mL to about 200 ng/mL, about 105 ng/mL to about 190 ng/mL, about 110 ng/mL to about 180 ng/mL, about 115 ng/mL to about 170 ng/mL, about 120 ng/mL to about 160 ng/mL, about 125 ng/mL to about 150 ng/mL, about 130 ng/mL to about 140 ng/mL, or about 135 ng/mL to about 140 ng/mL.

The term "reducing sugar" refers to any sugar that either has an aldehyde group or is capable of forming one in solution through isomerism. The reducing sugar may be a sugar that has reducing properties, and to a sugar that forms aldehyde or ketone in a basic solution. The reducing sugar may be, for example, a monosaccharide, maltose, lactose, sucrose, or fructose. The amount of reducing sugar used may vary according to the concentration ratio of the other elements of the sanal culturing composition. In some embodiments, the reducing sugar may be, for example, glucose. The reducing sugar may be present at a concentration of about 100 mg/L to about 600 mg/L, about 150 mg/L to about 600 mg/L, about 200 mg/L to about 600 mg/L, about 250 mg/L to about 550 mg/L, about 300 mg/L to about 500 mg/L, about 300 mg/L to about 450 mg/L, about 300 mg/L to about 400 mg/L, or about 355 mg/L.

The sanal culturing composition may be synthetic, and may further comprise some or all components of a minimal medium. The minimal medium refers to a synthetic medium comprising the minimal nutrients necessary for the proliferation or survival of cells or microcells. The minimal medium may be minimum essential medium (MEM). MEM is commercially available. The minimal medium may contain amino acids, vitamins (e.g., ascorbic acid, biotin, choline chloride, D-calcium pantothenate, folic acid, niacinamide, pyridoxal hydrochloride, riboflavin, thiamine hydrochloride, vitamin B12, and i-inositol), inorganic salts (e.g., calcium chloride, magnesium sulfate, potassium chloride, sodium bicarbonate sodium chloride, and sodium phosphate monobasic), ribonucleosides, deoxyribonucleosides, glucose, lipoic acid, sodium pyruvate, or a combination thereof (Proc. Natl. Acad. Sci. U.S.A., Simonsen, C. C. and Levinson, A. D. vol. 80, pp. 2495-2499, 1983).

Another embodiment of the present disclosure provides a method for culturing sanal, comprising culturing sanal in the presence of a sanal culturing composition as described herein.

The culturing step may comprise incubating sanal in the presence of a sanal culturing composition. The temperature of culture may be from about 25° C. to about 45° C., about 30° C. to about 40° C., about 35° C. to about 40° C., or about 37° C. The duration of culture may be about 1 hour or longer, about 6 hours or longer, about 12 hours or longer, about 1 day or longer, about 3 days or longer, or about 1 week or longer. The medium may be periodically replaced with a fresh medium during culture.

A stable in vitro proliferation or survival of sanals can be achieved using the sanal culturing composition and the sanal culturing method using the same.

The present disclosure is described in greater detail through the examples provided below. However, these examples are intended only to illustrate the present disclosure, and therefore, the scope of the present disclosure is not restricted to these examples.

Example 1. Preparation of Sanal Culture Fluid 1.1 Collecting Primo Ducts and Primo Nodes As sanal exists on the inside of a primo duct or a primo node, it would be possible to culture sanal in a culture fluid which has a composition similar to that of primo fluid in primo ducts. Thus, primo ducts and primo nodes distributed over the surface of internal organs were collected from rats in order to identify the composition of amino acids and sugars in primo fluid.

Rats used in the experiment were irradiated with light in such a manner that 12-hour periods of light and dark alternated, while they were confined in a constant temperature and humidity room which maintained a temperature of 23° C. and a relative humidity of 60%. The tested animals were allowed to have water and food freely without any constraints and were kept in an optimal condition for breeding, in accordance with the Seoul National University's codes of ethics for the treatment of laboratory animals, established in 1996. The rats used in dissection experiment were anesthetized by injecting 1.5 g/kg of urethane into the peritoneum. All dissection procedures were performed in a normal environment for anesthesia. An incision was made to the rat abdomen while the rat was under deep anesthesia, and phosphate-buffered saline (PBS, pH 7.4, Invitrogen, USA) was frequently sprayed onto the rat organs so as to prevent drying during dissection surgery. Primo ducts and primo nodes, which formed a white stem on the surface of the rat large intestine, were obtained.

0.5 mL of PBS was added to the obtained primo ducts and primo nodes, which were then chopped using a 1-mL syringe (Kovax-Syringe, Korea Vaccine Co., LTD). The chopped primo ducts and primo nodes were vortexed at 25° C. for 10 minutes and centrifuged at 4° C. for 30 minutes at a speed of 20,000×g, and thereafter, the supernatant and the pellet were separated. The supernatant was filtered using an Acrodisc Syringe Filter (Life Sciences, 0.2 μm Supor Membrane), and thereafter, the primo fluid was obtained. The pellet is cytosol of primo ducts and primo nodes.

1.2 Assaying Amino Acid Components in Primo Fluid

The composition of amino acids in primo fluid was assayed according to the method presented below.

Specifically, the solution obtained in Example 1.1 was assayed by the methods of high-performance liquid chromatography (HPLC) and nano liquid chromatography (LC), using a High-Performance Liquid Chromatograph 4 (Ultimate 3000, Thermo Dionex, USA). A high-pressure pump was used to pass the sample through a column at a high flow rate, and the sample was separated according to the difference in affinity between the beads inside the column and the substances of the sample. Amino acids in the separated sample were detected using UV/VIS Diode Array Detector (190-200 nm, spectrum scanning) or Fluorescence Detector suitable for each amino acid.

Figure 2A:
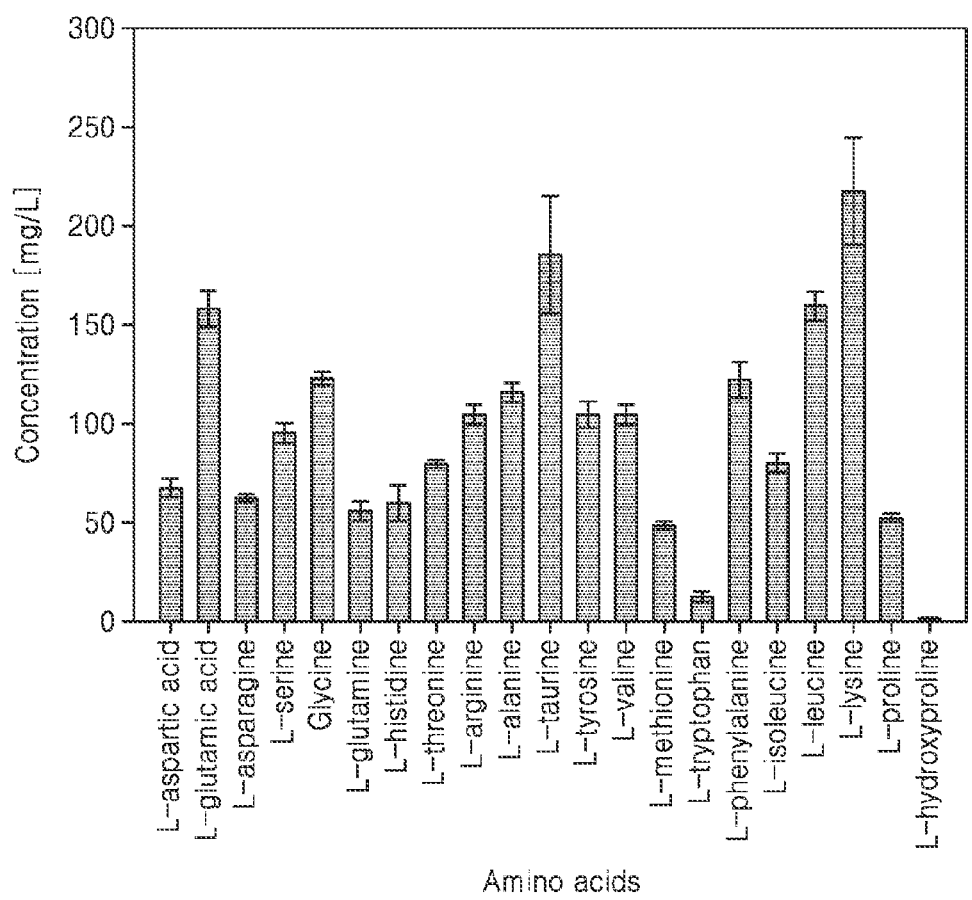
FIG. 2A is a graph showing the composition and concentration (mg/L) of amino acids in primo fluid.
Figure 2B:
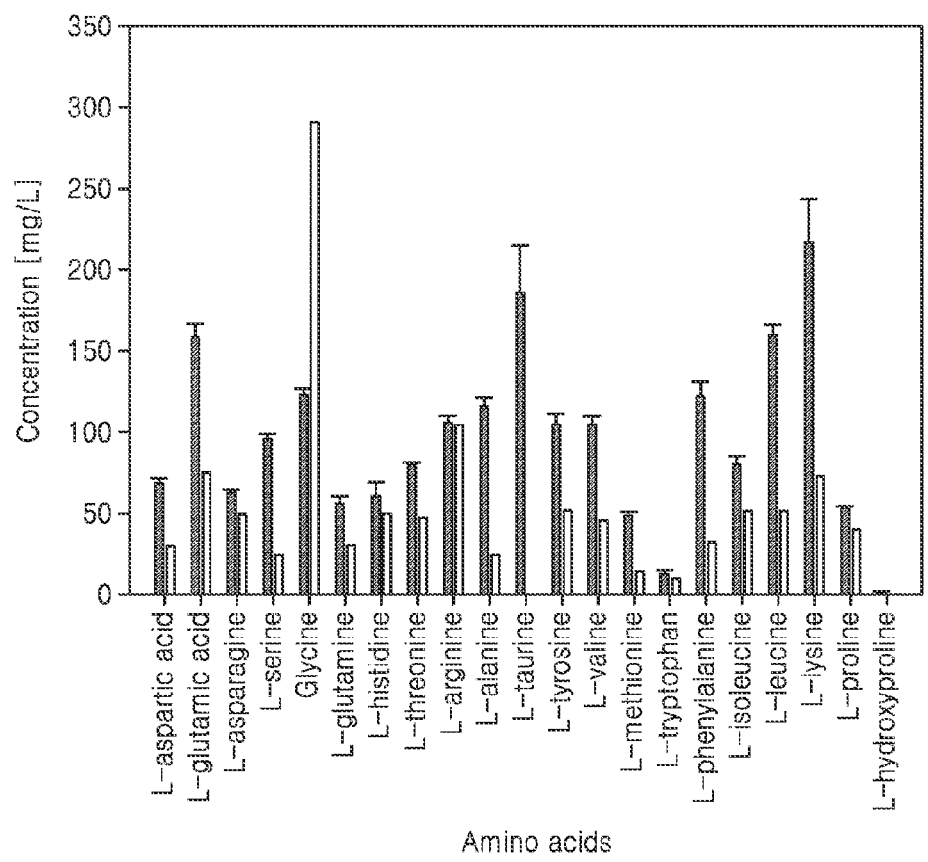
FIG. 2B is a graph comparing the composition and concentration (mg/L) of amino acids in primo fluid with the composition and concentration (mg/L) of amino acids in MEM culture medium (shaded bar: primo fluid, white bar: MEM culture medium)

The concentrations of amino acids in primo fluid were measured, and the results are illustrated in FIG. 2A. In addition, FIG. 2B illustrates a comparison of the composition and concentration of amino acids in primo fluid with the composition and concentration of amino acids in a MEM alpha (Gibco® Life Technologies, Cat. No. 41061) (shaded bar: primo fluid, white bar: MEM).

Figure 2C:
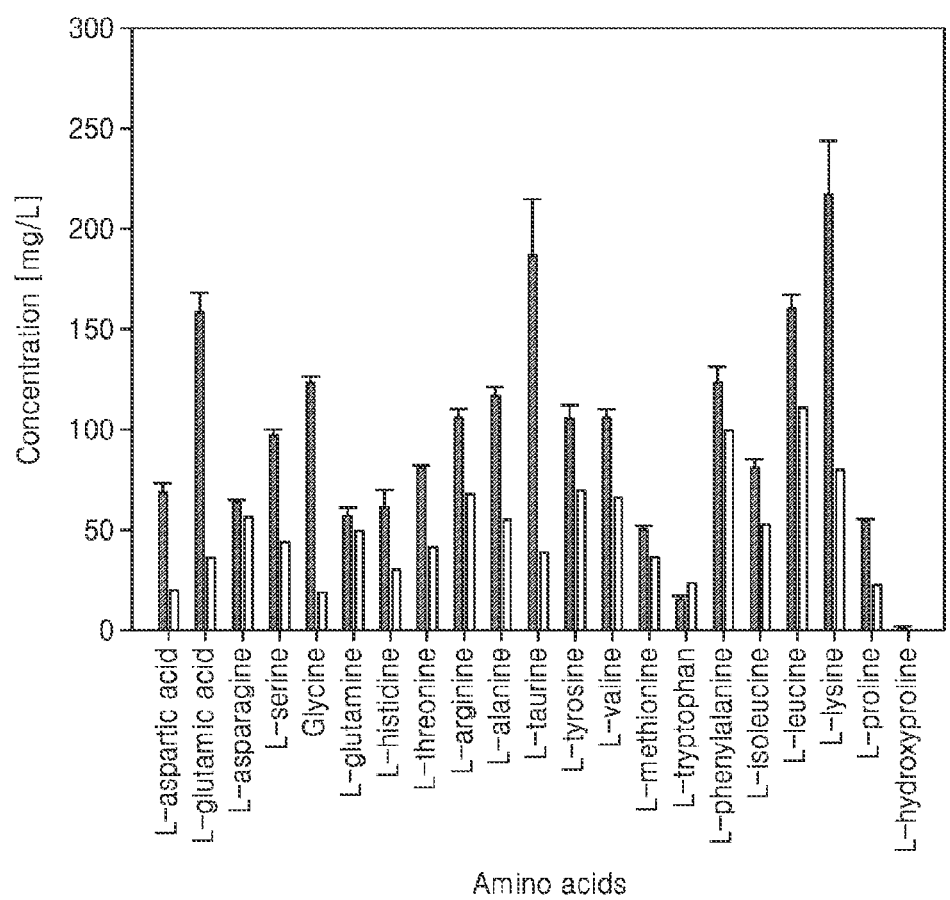
FIG. 2C is a graph showing the composition and concentration (mg/L) of amino acids in primo fluid and in cytosol of primo ducts and primo nodes (shaded bar: primo fluid, white bar: cytosol of primo ducts and primo nodes).

Furthermore, the amino acids present in the cytosol of primo ducts and primo nodes obtained in Example 1.1 were assayed by HPLC and nano LC, using a High-Performance Liquid Chromatograph 4 (Ultimate 3000, Thermo Dionex, USA). FIG. 2C illustrates a comparison of the composition amino acids in primo fluid with the composition of amino acids in cytosol of primo ducts and primo nodes (shaded bar: primo fluid, white bar: cytosol of primo ducts and primo nodes).

Table 1 below shows a comparison of the composition and concentration of amino acids in primo fluid, interstitial fluid, lymphatic fluid, and blood plasma, which are obtained from the rats used in the experiment in Example 1.1.

TABLE 1

| Amino Acid (mg/L) | Primo Fluid (n = 5) | Interstitial Fluid | Lymphatic Fluid | Blood Plasma |
| --- | --- | --- | --- | --- |
| L-Aspartic acid | 68.3 ± 4.34 | 1.13 | 171.6287 | 3.6 |
| L-Glutamic acid | 157.9 ± 9.63 | 10.382 | 250.8982 | 21.6 |
| L-Asparagine | 63.1 ± 1.80 | 3.849 | 27.2493 | 7.8 |
| L-Serine | 96.1 ± 3.99 | 7.833 | 40.577 | 17.9 |
| Glycine | 123.8 ± 2.57 | 7.85 | 79.963 | 1.7 |
| L-Glutamine | 56.2 ± 4.42 | 42.97 | 135.8612 | 10.7 |
| L-Histidine | 60.5 ± 9.03 | 3.105 | 15.9813 | 10.7 |
| L-Threonine | 80.4 ± 1.32 | 8.195 | 36.339 | 32.5 |
| L-Arginine | 105.6 ± 4.13 | 10.885 | 44.426 | 35.7 |
| L-Alanine | 116.0 ± 5.17 | 12.076 | 70.3837 | 37.4 |
| L-Taurine | 186.0 ± 29.6 | 7.977 | 214.3337 | 0 |
| L-Tyrisine | 104.6 ± 7.05 | 6.112 | 284.262 | 14.9 |
| L-Valine | 105.0 ± 4.48 | 6.631 | 35.7542 | 24 |
| L-Methionine | 49.6 ± 1.23 | 2.809 | 15.4886 | 9 |
| L-Tryptophane | 13.5 ± 2.17 | 1.659 | 3.1684 | 25.1 |
| L-Phenylalanine | 122.2 ± 8.91 | 4.38 | 32.7854 | 11.6 |
| L-Isoleucine | 80.3 ± 5.14 | 4.337 | 23.4005 | 13.1 |
| L-Leucine | 159.9 ± 6.99 | 7.501 | 45.0431 | 22.8 |
| L-Lysine | 217.8 ± 26.6 | 20.231 | 73.6931 | 58.9 |
| L-Proline | 53.5 ± 1.51 | 4.149 | 31.9353 | 18.8 |
| L-Hydroxyproline | 2.17 ± 0.50 | 1.021 | 3.273 | 7.2 |

As illustrated in FIGS. 2A and 2B, the amino acid composition of primo fluid was similar to the amino acid composition of MEM alpha (Gibco® Life Technologies, Cat. No. 41061), but the concentrations of glycine, taurine, and lysine of primo fluid was significantly different from concentrations of glycine, taurine, and lysine of MEM alpha. In addition, as illustrated in FIG. 2C, the concentration of amino acids present in the cytosol of primo ducts and primo nodes was found to be considerably lower than that present in primo fluid; however, the compositions were found to contain the same amino acids, differing only concentration. Moreover, the results of a comparison of primo fluid, interstitial fluid, lymphatic fluid, and blood plasma, as shown in Table 1, indicate that primo fluid had relatively high contents of lysine and taurine.

1.3 Assaying Hyaluronic Acid in Primo Fluid

The concentration of hyaluronic acid in primo fluid was assayed according to the method presented below.

Specifically, the solution obtained in Example 1.1 was subjected to reaction using a Quantikine ELISA Kit (Hyaluronan Immunoassay, Catalog Number DHYAL0), and the concentration of hyaluronic acid was measured using a microplate reader (Thermo Labsystems, Multiskan EX). The measured concentration of hyaluronic acid is illustrated in FIG. 3.

Figure 3:
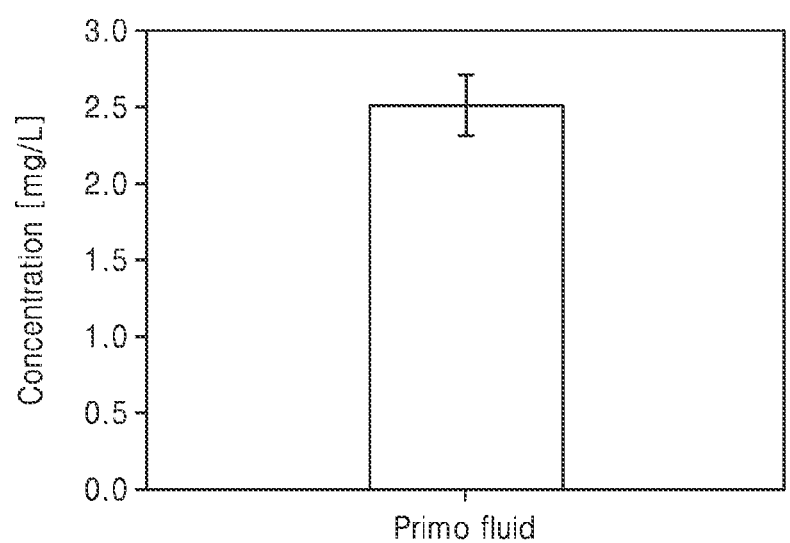
FIG. 3 is a graph showing the concentration of hyaluronic acid (mg/L) in primo fluid

As shown in FIG. 3, the concentration of hyaluronic acid in primo fluid was found to be about 2.5 mg/L.

1.4 Assaying Adrenalin and Noradrenaline in Primo Fluid

The concentrations of adrenalin and noradrenaline in primo fluid were assayed according to the method presented below.

Specifically, the solution obtained in Example 1.1, urine, blood plasma, and lymphatic fluid were subjected to reaction using an Epinephrine/Norepinephrine ELISA Kit (Abnova, Catalog Number KA1877), and the concentrations of adrenalin and noradrenaline were measured using a microplate reader (Thermo Labsystems, Multiskan EX). The measured concentrations of adrenalin and noradrenaline are illustrated in FIG. 4 and FIG. 5, respectively.

Figure 4:
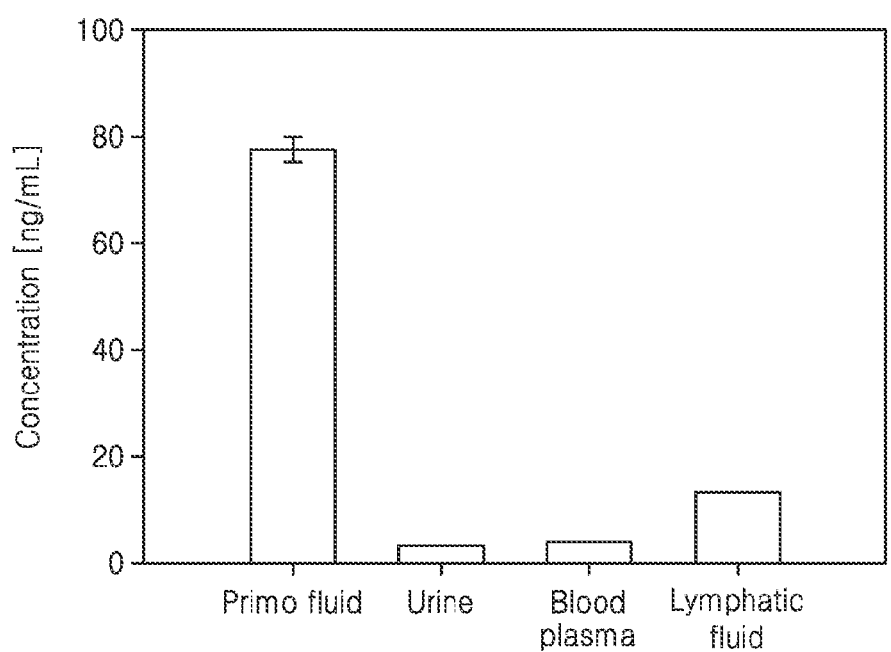
FIG. 4 is a graph showing the concentration of adrenalin (ng/mL) in primo fluid, urine, blood plasma, or lymphatic fluid.

As shown in FIG. 4, the concentration of adrenalin in primo fluid was about 78 ng/mL. The concentration of adrenalin in primo fluid was at least about 15 times the concentration of adrenalin in urine or in blood plasma, and at least about four times the concentration of adrenalin in lymphatic fluid.

Figure 5:
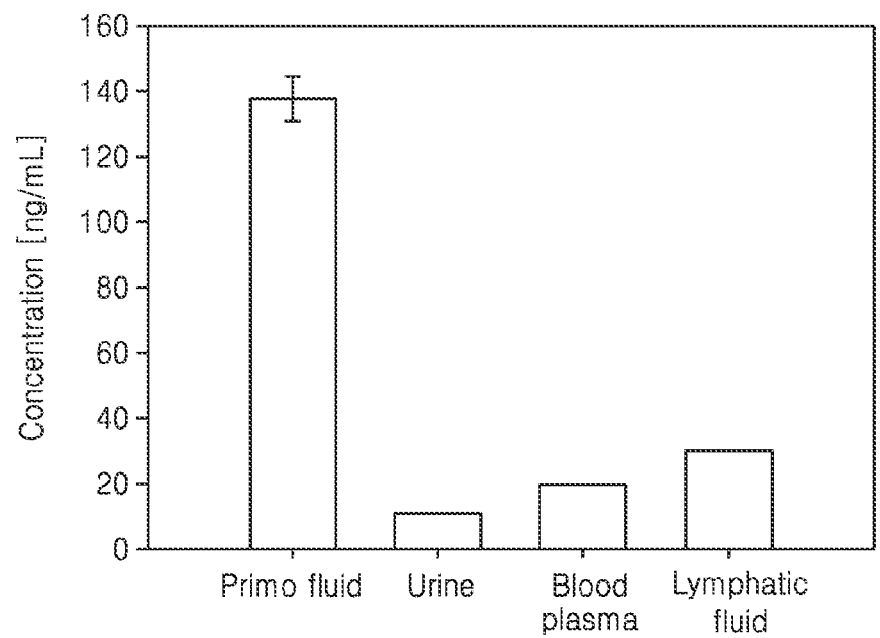
FIG. 5 is a graph showing the concentration of noradrenaline (ng/mL) in primo fluid, urine, blood plasma, or lymphatic fluid.

As shown in FIG. 5, the concentration of noradrenaline in primo fluid was about 138 ng/mL. The concentration of noradrenaline in primo fluid was at least about 13 times the concentration of noradrenaline in urine, at least about 6.5 times the concentration of noradrenaline in blood plasma, and at least about four times the concentration of noradrenaline in lymphatic fluid.

Thus, the concentrations of adrenalin and noradrenaline in primo fluid were found to be considerably higher than those in urine, blood plasma, and lymphatic fluid 1.5 Assaying Reducing Sugars in Primo Fluid The concentration of reducing sugars in primo fluid was assayed according to the method presented below.

Specifically, the solution obtained in Example 1.1 was assayed using a High-Performance Liquid Chromatograph 1 (Ultimate 3000, Thermo Dionex, USA). A high-pressure pump was used to pass the sample through a column at a high flow rate, and the sample was separated according to the difference in affinity between the beads inside the column and the substances of the sample.

Figure 6:
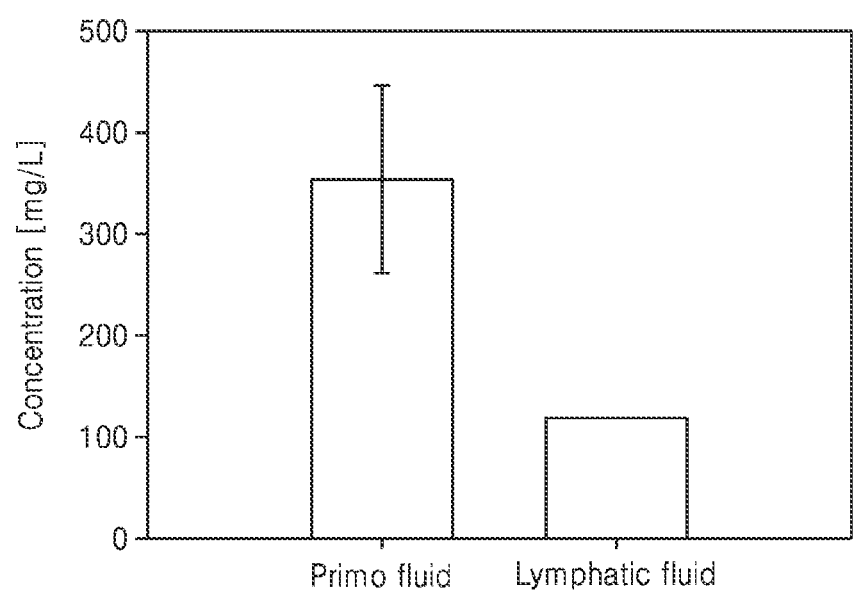
FIG. 6 is a graph showing the concentration of glucose (mg/L) in primo fluid or lymphatic fluid.

The concentration of glucose, a reducing sugar, measured from primo fluid and lymphatic fluid is illustrated in FIG. 6. As shown in FIG. 6, the amount of glucose in primo fluid was about 355±93.30 mg/L (n=3), and the amount of glucose in lymphatic fluid was about 119.68 mg/L. Thus, the amount of glucose in primo fluid was about three times the amount of glucose in lymphatic fluid.

It should be understood that the exemplary embodiments described herein should be considered in a descriptive sense only and not for purposes of limitation. Descriptions of features or aspects within each embodiment should typically be considered as available for other similar features or aspects in other embodiments.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method for culturing sanal in vitro, comprising culturing sanal in the presence of a sanal culturing composition comprising lysine, taurine, and hyaluronic acid.

2. The method for culturing sanal according to claim 1, wherein lysine is present in the sanal culturing composition at a concentration of about 150 mg/L to about 300 mg/L.

3. The method for culturing sanal according to claim 1, wherein taurine is present in the sanal culturing composition at a concentration of about 100 mg/L to about 300 mg/L.

4. The method for culturing sanal according to claim 1, wherein hyaluronic acid is present in the sanal culturing composition at a concentration of about 1 mg/L to about 5 mg/L.

5. The method for culturing sanal according to claim 1, wherein the sanal culturing composition further comprises hydroxyproline, adrenalin, noradrenaline, a reducing sugar, or a combination thereof.

6. The method for culturing sanal according to claim 5, wherein hydroxyproline is present in the sanal culturing composition at a concentration of about 1 mg/L to about 10 mg/L.

7. The method for culturing sanal according to claim 5, wherein adrenalin is present in the sanal culturing composition at a concentration of about 50 ng/mL to about 100 ng/mL.

8. The method for culturing sanal according to claim 5, wherein noradrenaline is present in the sanal culturing composition at a concentration of about 100 ng/mL to about 200 ng/mL.

9. The method for culturing sanal according to claim 5, wherein the reducing sugar is glucose.

10. The method for culturing sanal according to claim 5, wherein the reducing sugar is present in the sanal culturing composition at a concentration of about 100 mg/L to about 600 mg/L.

11. The method for culturing sanal according to claim 1, wherein the sanal culturing composition further comprises a minimal medium.

12. The method for culturing sanal according to claim 11, wherein the minimal medium comprises inorganic salts, amino acids, vitamins, glucose, or a combination thereof.

* * * * *